United States Patent [19]

McDaniel et al.

[11] Patent Number: 4,822,475
[45] Date of Patent: Apr. 18, 1989

[54] METHOD FOR DETERMINING THE FOULING TENDENCY OF CRUDE PETROLEUM OILS

[75] Inventors: Cato R. McDaniel; W. John Delaney, both of The Woodlands; Bruce E. Wright, Spring, all of Tex.

[73] Assignee: Betz Laboratories, Inc., Trevose, Pa.

[21] Appl. No.: 165,653

[22] Filed: Mar. 8, 1988

[51] Int. Cl.$^4$ .................. C10G 9/12; C10G 9/16; G01N 33/24
[52] U.S. Cl. .................. 208/48 AA; 208/48 R; 436/60; 436/139
[58] Field of Search ............. 208/48 AA; 436/60, 139

[56] References Cited

U.S. PATENT DOCUMENTS

| | | | |
|---|---|---|---|
| 2,732,285 | 1/1956 | Lynch et al. | 436/60 |
| 3,087,888 | 4/1963 | Saraceno | 208/251 |
| 3,438,735 | 4/1969 | Doyle | 23/230 |
| 3,856,664 | 12/1974 | Whitehurst | 208/253 |
| 4,115,063 | 9/1978 | Demers | 23/230 M |
| 4,238,451 | 12/1980 | Crais et al. | 436/139 |
| 4,388,408 | 6/1983 | Sien et al. | 436/60 |
| 4,412,007 | 10/1983 | Yong et al. | 436/135 |
| 4,556,326 | 12/1985 | Kitchen, III et al. | 374/45 |
| 4,578,178 | 3/1986 | Forester | 208/48 AA |

FOREIGN PATENT DOCUMENTS

| | | | |
|---|---|---|---|
| 0241233 | 10/1987 | European Pat. Off. | 436/60 |
| 0236066 | 11/1985 | Japan | 436/60 |

OTHER PUBLICATIONS

Knudsen, "Apparatus and Techniques for Measurement of Fouling of Heat Transfer Surfaces", *Fouling of Heat Transfer Equipment*, Somerscales et al., Editors, Hemisphere Pub. Corp., New York (1981), pp. 57-81.

Hagney, "The Evaluation and Application of Metal-Coordinating Anti-Foulants", Betz Laboratories, Inc., Technical Paper 210 (1970), no month indicated.

Braun, "The Nature of Petroleum Process Fouling—Results of a Practical Instrument", *Corrosion/77* (San Francisco Hilton Hotel, San Francisco, Calif., Mar. 14-18, 1977).

*Primary Examiner*—H. M. S. Sneed
*Assistant Examiner*—Helane Myers
*Attorney, Agent, or Firm*—Alexander D. Ricci; Charlotte M. Kraebel

[57] ABSTRACT

This invention relates to a process for determining the fouling tendency of a crude petroleum oil feed, comprising the steps of:

(a) mixing a selected volume of crude petroleum oil sample with a selected volume of a solvent medium, (b) agitating the resulting mixture to solubilize fouling-determining materials in the solvent medium, (c) removing a sample of the resulting solvent medium, (d) determining absorbance of the resulting solvent medium at 230-270 nm and subtracting from the absorbance that of control solvent medium to obtain corrected absorbance of the resulting solvent medium and (e) determining the fouling tendency of the crude petroleum oil sample by correlating the corrected absorbance of the resulting solvent medium with calibration data specific for the solvent medium used, the ratio of oil sample to polar solvent and the wavelength at which absorbance is determined.

The thus-determined fouling tendency can be used to predict the amount of antifouling agent, required to prevent fouling during downstream processing.

24 Claims, 3 Drawing Sheets

4,822,475

METHOD FOR DETERMINING THE FOULING TENDENCY OF CRUDE PETROLEUM OILS

TECHNICAL FIELD

This invention relates to a process for determining the fouling tendency of crude petroleum oils. This invention further relates to a process for refining crude petroleum oils wherein the amount of antifouling agent, added during processing, is adjusted to compensate for variations in the fouling tendency of the feed.

BACKGROUND ART

During processing of hydrocarbon feeds, including petroleum hydrocarbons, petroleum feedstocks, petroleum processing intermediates, petrochemicals or petrochemical intermediates, including gas, oils and reformer stocks, chlorinated hydrocarbons, olefin plant fluids and deethanizer bottoms, the hydrocarbon feeds are customarily heated to temperatures of 40° to 550° C. The foregoing petroleum hydrocarbons or feedstocks are also used as heating media on the "hot side" of heating and heat exchange systems. Whenever petroleum hydrocarbon materials are subjected to high temperatures, a separate phase, known as fouling deposits, is produced from the petroleum hydrocarbon materials.

Fouling deposits are always considered to be highly undesirable by-products because:

(a) fouling deposits can reduce the diameter of pipes and conduits or vessels and cause a decrease in feed throughput, loss of capacity and decrease in process yields;

(b) fouling deposits impair thermal transfer, for example, in heat exchanger systems and furnaces, by forming an insulating layer on the heating surface, which layer both restricts heat transfer and results in the need for frequent shut-downs for cleaning; and (c) fouling deposits can damage equipment, necessitating replacement thereof.

Although the nature of the fouling deposits is not completely understood, the deposits appear to contain coke-like carbonaceous deposits, polymers or condensates, solids and salt formations. The salt formations are primarily magnesium, calcium and sodium salts. The formation of carbon condensates is believed to be catalyzed by heavy metal impurities in the hydrocarbon feedstock, for example, by compounds of copper or iron. The heavy metal contaminants may also deleteriously affect hydrocarbon processing by increasing the rate of degenerative chain branching to form free radicals. The free radicals can initiate oxidation and polymerization reactions, which produce gums and sediments. It is also thought that the thus-produced gums and sediments entrain relatively more inert carbonaceous deposits to produce thicker fouling deposits and higher insulating effects than otherwise.

Fouling is also a problem in processes for making or purifying petrochemicals. For example, deposits which are primarily polymeric, are produced during processing of monomers such as ethylene or propylene or purification of feeds such as chlorinated hydrocarbons.

The formation of fouling deposits can be reduced by adding antifouling additives to the hydrocarbon feed prior to or during processing. Typical antifouling additives are those disclosed by Forester, U.S. Pat. No. 4,578,178, herein incorporated by reference. This reference describes a commonly-used test for testing fouling characteristics of feeds. The test comprises pumping process fluid from a pressure vessel through a heat exchanger, containing an electrically-heated rod. The process fluid is then cooled to room temperature in a water-cooled condenser and remixed with the fluid in the pressure vessel. The system is maintained under nitrogen pressure in order to minimize vaporization of the process fluid.

The temperature of the rod is controlled at a preselected temperature. However, as fouling occurs, less heat is transferred to the process fluid and the temperature of the fluid leaving the heat exchanger decreases. The decrease in effluent temperature therefore correlates empirically with the fouling tendency or fouling potential of the hydrocarbon feed.

In an alternative testing procedure, the temperature of the effluent process fluid from the pressure vessel is maintained constant by increasing the power to the rod in response to variations in the temperature of the effluent. The degree of fouling is proportional to the increase in rod temperature, compared to that of a control rod. Both methods of evaluating fouling are variations of the fouling rig test. Although results of the fouling rig tests provide a high degree of correlation with fouling tendencies of the material being evaluated, the test methods are neither rapid nor simple to operate.

Whitehurst, in U.S. Pat. No. 3,856,664, has proposed determining the extent of removal of heavy metals from liquids, such as gasoline, by measuring the transmittance or absorbance at 425 nm.

Kitchen, III, et al. (U.S. Pat. No. 4,556,326) have recited testing fuel, subjected to accelerated ageing, by measuring transmittance at 527 nm.

Sien, in U.S. Pat. No. 4,388,408, has recited evaluating the suitability of coker feedstock by a process in which absorption chromatography and ultraviolet light absorptivity are employed.

Demers has proposed (U.S. Pat. No. 4,115,063) determining the total metal content of an organic solvent by a process including an extraction step and flame photometry or atomic absorption spectroscopy.

Saraceno, in U.S. Pat. No. 3,087,888, has proposed determining the vanadium content of an oil sample, using electron paramagnetic spectroscopy.

Doyle (U.S. Pat. No. 3,438,735) has proposed a colorimetric method for determining removal of metals from oily materials.

It will be apparent that existing methods for determining the fouling tendencies of petroleum oils are limited to the cumbersome, slow fouling rig tests or are directed to a specific impurity in the hydrocarbon material, rather than to cumulative fouling tendency of the sample.

It is the object of this invention to provide a simple method for determining the fouling tendency of hydrocarbon feeds, such as petroleum oils, as well as to use the information generated to control fouling tendency in refineries and other process contexts, by providing guidance as to the amount of antifouling agent, needed to produce acceptable operating conditions.

SUMMARY OF THE INVENTION

In one aspect, this invention comprises a process for determining the fouling tendency of a crude petroleum oil, comprising the steps of:

(a) mixing a selected volume of crude petroleum oil sample with a selected volume of a solvent medium, (b) agitating the resulting mixture to solubilize fouling-determining materials in the solvent medium, (c) removing a sample of the resulting solvent medium, (d) determining the absorbance of the resulting solvent medium at 230-270 nm and subtracting from the absorbance that of control solvent medium to obtain corrected absorbance of the resulting solvent medium and (e) determining the fouling tendency of the crude petroleum oil sample by correlating the corrected absorbance of the resulting solvent medium with calibration data specific for the solvent medium used, the ratio of oil sample to solvent medium and the wavelength at which absorbance is determined.

In another aspect, this invention relates, in a process of refining a crude petroleum oil feed, containing varying amounts of fouling-inducing contaminants, to the improvements comprising:

(a) mixing a selected volume of crude petroleum oil sample with a selected volume of a solvent medium;

(b) agitating the resulting mixture to solubilize fouling-determining materials in the solvent medium;

(c) removing a sample of the resulting solvent medium;

(d) determining the absorbance of the resulting solvent medium at 230-270 nm and subtracting from the absorbance that of control solvent medium to obtain corrected absorbance of the resulting solvent medium;

(e) determining the fouling tendency of the crude petroleum oil sample by correlating the corrected absorbance of the resulting solvent medium with calibration data specific for the solvent medium used, the ratio of oil sample to solvent medium and the wavelength at which absorbance is determined; and (f) adding to the feed sufficient antifouling agent to compensate for the fouling tendency, determined in step (e).

"Crude petroleum oil feed," as used in the specification and claims, includes any hydrocarbon-based material or mixture which is subject to fouling during processing at elevated temperatures. These materials include, but are not limited to, petroleum hydrocarbons, petroleum processing intermediates, oils, reformer stocks and resides.

"Fouling tendency" means the tendency of the feed to form fouling deposits under the heating conditions employed. The fouling-inducing components in the feed can include vacuum bottoms and heavy ends, inorganic salts, sulfur, organic sulfur compounds, caustic, organo-metallic compounds, gum, wax, polymers and asphaltenes (hexane-insoluble materials), all of which, under some circumstances, increase the likelihood of fouling at elevated temperatures. However, there is no precise correlation between individual components of hydrocarbon feeds and fouling tendency. There are complex relationships between the amount of particular impurities, or combinations of impurities, in hydrocarbon feeds and fouling tendency at high temperatures. The overall fouling tendency has been found to be related to absorbance in the ultraviolet at 230-270 nm, particularly to absorbance at 254 nm.

A selected volume of the crude petroleum oil feed is mixed with a selected volume of solvent medium. "Solvent medium," as used in the specification and claims means any solvent, or combination of solvents, which has low or zero absorbance at 230-270 nm and which can solubilize fouling-determining materials. These solvents include, but are not limited to acetonitrile, methanol, ethanol, water, octane, isooctane, methylene chloride, ethers, fluorocarbons, n-butanol and tert-butanol, and mixtures thereof.

A preferred solvent medium is a mixture, containing 1-50% by volume of water and 99-50% by volume of acetonitrile. Also preferred as a solvent medium is isooctane. A combination of 1-50% by volume of water and 99-50% by volume of methanol is also preferred. Most preferably, the solvent medium is neat acetonitrile.

"Fouling-determining material," as used in the specification and claims, includes materials in the petroleum oil sample which affect the fouling tendency of the feed. These materials can include both fouling-inducing and fouling-retarding materials. The relationship between composition and absorbance at 230-270 nm has not been precisely determined, but there is significant correlation between absorbance at 230-270 nm and fouling tendency during high temperature processing.

The petroleum oil sample and solvent medium can be mixed in any proportions. However, it is preferred to use a volumetric excess of solvent medium to petroleum oil sample. Most preferably, the ratio of volumes of crude petroleum oil sample to solvent medium is 1:10 to 1:100,000.

The crude petroleum oil sample and solvent medium are contacted or agitated so that fouling-determining materials are solubilized in the solvent medium. This is preferably done by shaking or agitating the mixture. Phase separation can be accomplished by centrifugation. It will be understood that, to obtain reproducible results, the method of shaking or the conditions of centrifugation should be standardized within a series of tests, so that the results are internally consistent. However, the exact conditions for agitating the mixture can be determined by routine experimentation. The agitated mixture may separate into oil-containing and solvent-containing phases.

A sample of the solvent-containing phase is removed, so that absorbance can be measured at 230-270 nm. It is preferred to measure absorbance at 254 nm. Absorbance (A) means:

$$A = log_{10}(1/T) = log_{10}(P_o/P)$$

wherein T=transmittance, P=radiant power transmitted by sample and $P_o$=radiant power incident on sample. It will therefore be understood that transmittance or percent absorption or transmission can be measured, rather than absorbance, and that the results can be related to absorbance as above. The claims herein shall be construed to include absorbance, whether determined directly or indirectly.

It is preferred, however, to practice the principles of this invention using a scale absorbance, which is:

$$A_{scaled} = 100 - [(\text{absorbance of crude petroleum oil})/(\text{absorbance of low-fouling standard sample})] \times 100.$$

Absorbance can be measured in a single beam or double beam spectrophotometer. In either case, the measured absorbance is corrected for the absorbance of control polar solvent medium to obtain corrected absorbance:

$$A_{measured} - A_{control} = A_{corrected}.$$

When a single beam spectrophotometer is used, the absorbance of the sample and of control solvent medium can be measured in either order. When a double beam instrument is used, the absorbance of the sample and control are determined simultaneously and $A_{corrected}$ can be read directly. This corrected absorbance value is correlated with calibration data specific for the solvent medium used, the ratio of oil sample to solvent medium and the wavelength at which absorbance is measured. It will be understood that the calibration data can be provided in the form of a plot of fouling vs. absorbance or can be in the form of a readout, provided by a spectrophotometer, programmed to make the required correlation.

The thus-determined fouling tendency is the basis upon which the plant operator selects the amount of antifouling agent to be added to the feed. Antifoulants, as disclosed by Forester, supra, or other known antifoulants can be added to the feed to adjust for changing feed fouling tendencies. Preferred conditions are otherwise as above. In using the method of this invention to control addition of antifouling agent, the process can be repeated at periodic intervals, or as necessitated by process conditions, including change of feed sources.

BEST MODE FOR CARRYING OUT THE INVENTION

Most preferably, the processes of this invention are those wherein the solvent medium is acetonitrile; the ratio of crude petroleum oil sample to solvent medium is 1;10 to 1:100,000 by volume; agitation is accomplished by shaking; separation is accomplished by centrifugation and absorbance is determined at 254 nm.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by volume.

EXAMPLE 1

A sample of crude oil (5 microliter) was added to 30 mL of acetonitrile:water 75:25 v/v solvent medium and mixed. The sample was centrifuged at 1500 rpm for 5 min, after which the clear liquid was removed. The absorbance of the clear liquid at 254 nm was measured in a quartz cuvette, as was the absorbance of a control sample of the solvent medium. The corrected absorbance was the difference between the absorbance of the sample and the absorbance of the control sample. A calibration curve was constructed by determining absorbance of crude oils, having known fouling rig values, under the same conditions.

Good correlation was observed for fouling values, measured by absorbance at 254 nm and by fouling rig tests.

EXAMPLE 2

Experiments were done as in Example 1, using the following solvent media:
(a) 95:5 acetonitrile:water,
(b) 50:50 acetonitrile:water,
(c) 50:50 methanol:water,
(d) 75:25 methanol:water,
(e) 95:5 methanol:water,
(f) 100% acetonitrile,
(h) 100% isooctane,
Similar results were obtained.

EXAMPLE 3

Experiments were done as in Example 1, using crude oil samples with known fouling ratings, determined by fouling rig tests.

Figure 1:
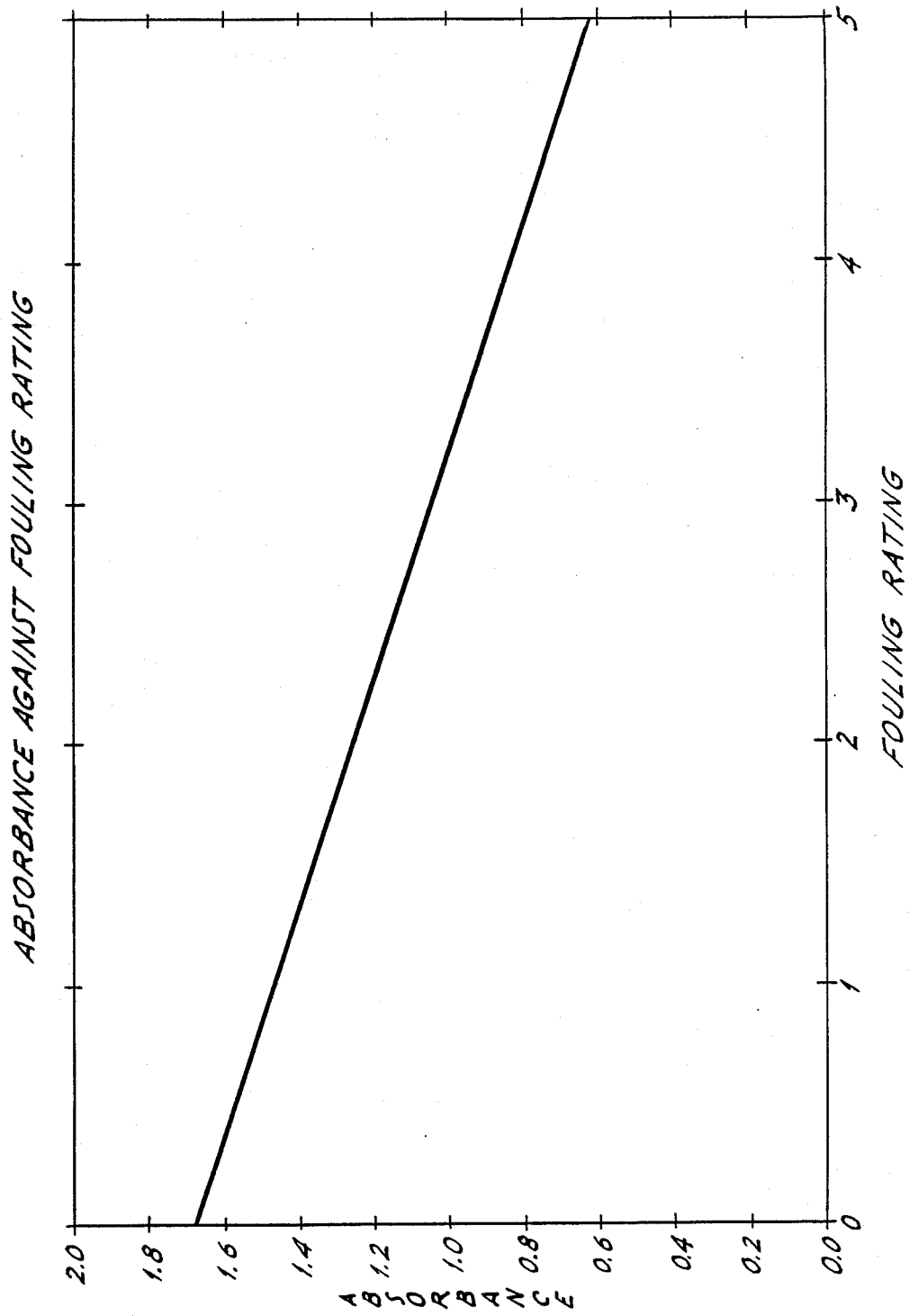
In FIG. 1 is shown the correlation between fouling tendencies of crudes, as measured by the fouling rig test and as measured by absorbance at 254 nm.

Results are given in Table 1 and in FIG. 1. The values given in Table 1 are scaled absorbance values, in which a low-fouling crude having a corrected absorbance of 1.94 at 254 nm was used as standard. These results show that oils having high absorbance at 254 nm were rated as low to moderate fouling (1-3 on scale of 5), whereas samples with low absorbance values were high fouling (4-5 fouling rating). Under the specific conditions used, 12 of 15 high fouling oils (80%) were predicted correctly and 26 of 27 low fouling oils (96%) were predicted correctly. When oils assigned a fouling rating of 3 were designated as low/moderate

TABLE 1

CRUDE OIL FOULING TENDENCIES AND ABSORBANCES

| REFINERY LOCATION | FOULING RATING | ABSORBANCE |
|---|---|---|
| WEST COAST | 1 | 1.94 |
| GULF COAST | 1 | 1.33 |
| ROCKY MOUNTAIN | 1 | 1.52 |
| GULF COAST | 1 | 1.09 |
| GULF COAST | 1 | 1.30 |
| GULF COAST | 1 | 1.21 |
| WEST COAST | 1 | 0.94 |
| GULF COAST | 1 | 1.05 |
| EAST COAST | 1 | 0.96 |
| WEST COAST | 1 | 1.55 |
| WEST COAST | 1 | 2.42 |
| GULF COAST | 1 | 1.48 |
| GULF COAST | 2 | 1.25 |
| GULF COAST | 2 | 1.17 |
| GULF COAST | 2 | 1.11 |
| MIDWEST | 2 | 1.15 |
| GULF COAST | 2 | 3.06 |
| WEST COAST | 2 | 1.35 |
| GULF COAST | 2 | 1.41 |
| MIDWEST | 2 | 1.31 |
| EAST COAST | 2 | 1.58 |
| GULF COAST | 2 | 0.90 |
| WEST COAST | 2 | 1.22 |
| GULF COAST | 2 | 1.46 |
| EAST COAST | 2 | 1.08 |
| EAST COAST | 2 | 0.97 |
| ROCKY MOUNTAIN | 3 | 0.91 |
| GULF COAST | 3 | 1.43 |
| GULF COAST | 3 | 0.88 |
| MIDWEST | 3 | 1.09 |
| GULF COAST | 3 | 1.30 |
| MIDWEST | 3 | 1.23 |
| MIDWEST | 3 | 1.17 |
| MIDWEST | 3 | 0.89 |
| GULF COAST | 3 | 1.34 |
| MIDWEST | 3 | 1.36 |
| GULF COAST | 3 | 1.04 |

TABLE 1-continued

CRUDE OIL FOULING TENDENCIES AND ABSORBANCES

| REFINERY LOCATION | FOULING RATING | ABSORBANCE |
| --- | --- | --- |
| GULF COAST | 3 | 0.92 |
| GULF COAST | 3 | 0.52 |
| ROCKY MOUNTAIN | 4 | 0.80 |
| MIDWEST | 4 | 0.98 |
| GULF COAST | 4 | 0.12 |
| GULF COAST | 4 | 0.23 |
| WEST COAST | 4 | 1.23 |
| AUSTRALIAN | 5 | 0.76 |
| MIDWEST | 5 | 0.98 |
| MIDWEST | 5 | 1.02 |
| ROCKY MOUNTAIN | 5 | 0.66 |
| ROCKY MOUNTAIN | 5 | 0.92 |
| ROCKY MOUNTAIN | 5 | 0.93 |
| ROCKY MOUNTAIN | 5 | 0.84 |
| GULF COAST | 5 | 0.13 | moderate fouling, the prediction of low/moderate fouling was correct in 36 of 40 cases (85%).

The slope of the plot of absorbance aginst fouling rating is $-0.18x+1.64$ in FIG. 1.

EXAMPLE 4

Crude oils, tested in fouling rig experiments, were characterized analytically. Selected parameters for which data were determined included API gravity, asphaltene content, sulfur content, metals content, viscosity. Parameters which correlate well with fouling severity included API gravity, sulfur content, solids content, neutralization number, asphaltene content and salt content. Results for lab fouling severities, field fouling tendency and various constituents of crude petroleum oils are given in Tables 2 and 3. These results show that heretofore, determination of fouling tendency of oils constituted a complex analytical task.

EXAMPLE 5

Figure 2:
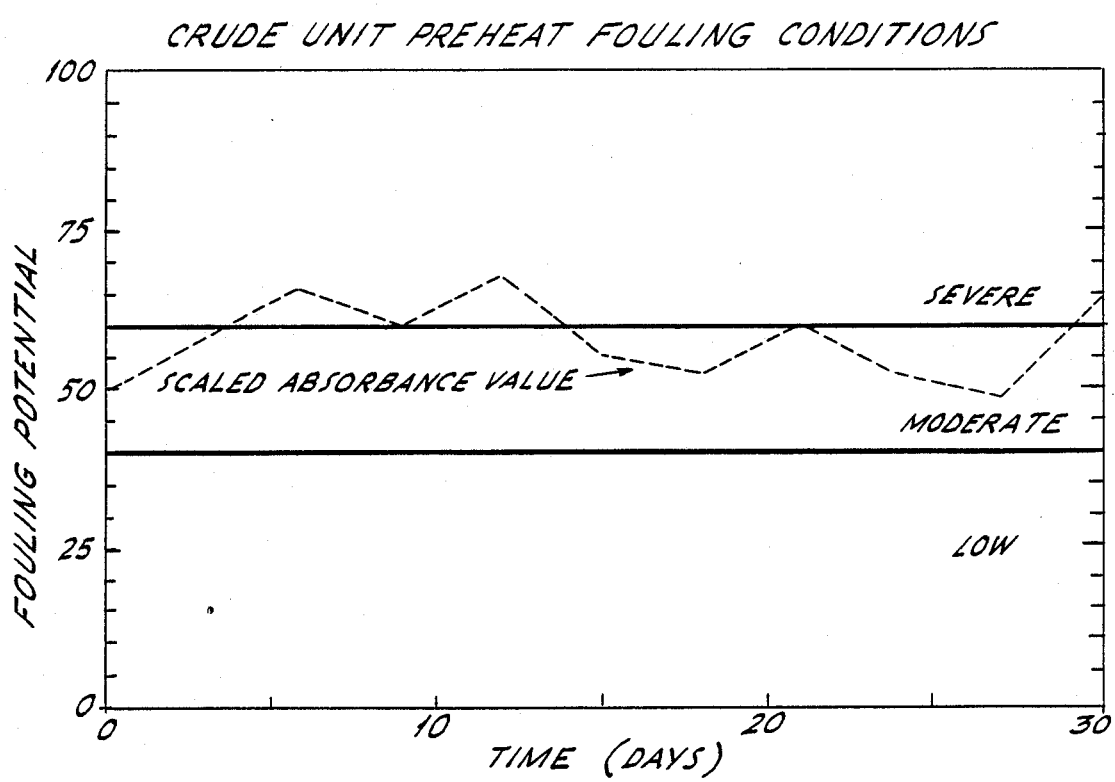
In FIG. 2-4 are shown results of refining runs, in which the amount of antifouling agent added is determined as a result of fouling tendency, related to absorbance, determined at 254 nm.

The process of the invention was used to predict fouling potential of a feed, which was normally severe, but inconsistent. By monitoring the fouling potential, as set forth in Example 1, and adjusting the dosage of antifouling additive, the refinery operator was able to save about 25% of its normal antifoulant costs, without sacrificing results. The scaled absorbance values of feeds entering this unit over a 30-day period are shown in FIG. 2.

EXAMPLE 6

Figure 3:
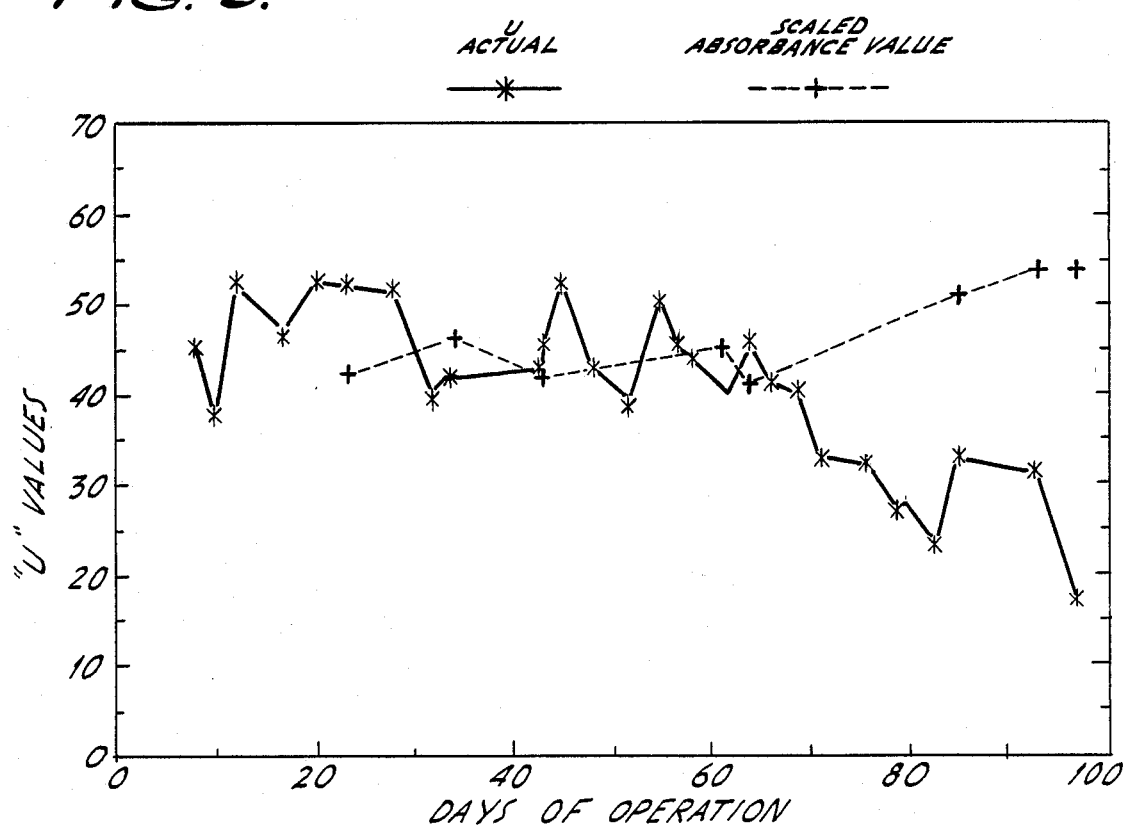

A refinery has successfully used antifoulant, at a low maintenance dosage. However, crudes that became available to the refinery recently had characteristics unlike those of prior crudes. As shown on FIG. 3, it was determined, using the process set forth in Example 1, that fouling severity (scaled absorbance values) were increasing over time. Antifoulant dosage remained constant in spite of the increase in the scaled absorbance values. As shown in FIG. 3, the heat transfer efficiency ("U") decreased and correlated with increasing scaled absorbance values, measured at 254 nm, in the absence of any change in the antifoulant dosage.

TABLE 2

FOULING TENDENCIES OF SELECTED CRUDE OILS

| CRUDE SLATE | FOULING SEVERITY* BASED ON LAB TESTS | FIELD FOULING TENDENCY |
| --- | --- | --- |
| 1 | 5 | High |
| 2 | 2 | Low |
| 3 | 4 | High |
| 4 | 3 | Moderate |
| 5 | 5 | High |
| 6 | 3 | Moderate |
| 7 | 4 | High |
| 8 | 5 | High |
| 9 | 2 | Moderate |
| 10 | 1 | Low |
| 11 | 2 | Moderate |
| 12 | 2 | Moderate |
| 13 | 2 | Moderate |
| 14 | 3 | Moderate |
| 15 | 1 | Low |
| 16 | 5 | High |
| 17 | 1 | Low |
| 18 | 2 | Moderate |
| 19 | 2 | Moderate |
| 20 | 2 | Moderate |
| 21 | 1 | Low |
| 22 | 1 | Low |
| 23 | 3 | Low/Moderate |
| 24 | 2 | Moderate |
| 25 | 1 | Moderate |
| 26 | 3 | High |
| 27 | 2 | Low |
| 28 | 1 | Low |
| 29 | 2 | Low |
| 30 | 1 | Low |
| 31 | 2 | Moderate |
| 32 | 4 | Moderate |

*1 = Low Severity
5 = Very High Severity

TABLE 3

CRUDE OIL DATA BASE ANALYSES

| CRUDE SLATE | FOULING RATING | API GRAVITY | SALT (PTB) | FILTERABLE SOLIDS | SULFUR (WT %) | MERCAPTANS (PPM) | NEUT # (mg KOH/gm) | ASPHALTENES (Wt %) | CONRADSON CARBON (WT %) |
| --- | --- | --- | --- | --- | --- | --- | --- | --- | --- |
| 1 | 5 | 45.7 | 2.4 | 18.2 | 0.1 | 14 | 1.8 | 0.1 | 0.3 |
| 2 | 2 | 36.8 | 1.4 | 15.4 | 0.2 | 50 | 0.8 | 0.5 | 1.6 |
| 3 | 4 | 38.8 | 0.4 | 7.7 | 0.2 | 32 | 0.5 | 0.1 | 1.4 |
| 4 | 3 | 30.5 | 0.1 | 6.3 | 1.8 | 43 | 1.4 | 2.2 | 7.1 |
| 5 | 5 | 39.9 | 0.5 | 27.3 | 0.4 | 64 | 1.3 | 0.3 | 1.6 |
| 6 | 3 | 40.9 | 0.6 | 14.1 | 0.4 | 47 | 0.9 | 0.4 | 1.3 |
| 7 | 4 | 35.7 | 0.1 | 21.7 | 0.9 | 51 | 0.6 | 0.3 | 2.6 |
| 8 | 5 | 41.9 | 4.7 | 39.9 | 0.04 | 32 | 0.8 | 0.4 | 0.9 |
| 9 | 2 | 35.0 | 0.7 | 12.6 | 1.1 | 21 | 0.1 | 0.4 | 1.5 |
| 10 | 1 | 23.5 | 3.6 | 24.5 | 3.8 | 65 | 0.1 | 1.0 | 6.8 |
| 11 | 2 | 34.1 | 1.8 | 8.4 | 0.4 | 30 | 0.8 | 0.6 | 2.1 |
| 12 | 2 | 24.6 | 7.7 | 105.0 | 1.6 | 224 | 0.7 | 3.6 | 5.7 |
| 13 | 2 | 23.2 | 0.7 | 39.9 | 2.0 | 448 | 0.6 | 5.2 | 9.0 |
| 14 | 3 | 32.1 | 0.5 | 42.7 | 1.5 | 50 | 1.6 | 2.1 | 3.3 |
| 15 | 1 | 33.5 | 0.1 | 14.0 | 0.4 | 14 | 1.3 | 0.8 | 2.4 |
| 16 | 5 | 61.6 | 0.1 | 11.2 | 0.1 | 15 | 0.2 | 0.7 | 0.1 |
| 17 | 1 | 28.7 | 0.5 | 8.4 | 2.1 | 50 | 1.0 | 6.9 | 7.1 |
| 18 | 2 | 31.5 | 0.1 | 8.4 | 1.8 | 59 | 0.1 | 0.8 | 4.6 |

TABLE 3-continued

CRUDE OIL DATA BASE ANALYSES

| | | | | | | | | | |
|---|---|---|---|---|---|---|---|---|---|
| 19 | 2 | 29.5 | 21.9 | 7.0 | 2.0 | 81 | 0.9 | 4.9 | 7.6 |
| 20 | 2 | 27.1 | 1.0 | 11.9 | 1.8 | 32 | 1.4 | 4.3 | 7.1 |
| 21 | 1 | 16.7 | 0.9 | 14.0 | 1.1 | 448 | 4.9 | 2.6 | 8.6 |
| 22 | 1 | 34.3 | 1.4 | 37.1 | 0.3 | 8 | 2.2 | 0.2 | 1.6 |
| 23 | 3 | 36.5 | 0.1 | 11.2 | 0.2 | 50 | 1.5 | 0.1 | 0.9 |
| 24 | 2 | 24.2 | 0.2 | 11.9 | 0.4 | 88 | 2.1 | 0.01 | 1.8 |
| 25 | 1 | 29.5 | 0.2 | 10.5 | 0.7 | 35 | 1.8 | 3.6 | 8.0 |
| 26 | 3 | 36.0 | 0.1 | 14.0 | 0.8 | 16 | 0.4 | 0.02 | 0.4 |
| 27 | 2 | 36.9 | 0.1 | 15.4 | 0.6 | 41 | 0.6 | 0.3 | 1.8 |
| 28 | 1 | 26.2 | 1.6 | 9.1 | 0.9 | 32 | 0.7 | 2.0 | 5.4 |
| 29 | 2 | 33.8 | 52.4 | 63.0 | 1.2 | 50 | 1.6 | 0.4 | 4.3 |
| 30 | 1 | 27.4 | 0.3 | 9.8 | 1.4 | 214 | 0.5 | 2.8 | 5.7 |
| 31 | 2 | 22.9 | 1.6 | 6.3 | 2.4 | 50 | 2.9 | 8.6 | 9.5 |
| 32 | 4 | 45.2 | 0.1 | 5.6 | 0.2 | 36 | 0.7 | 1.1 | 1.4 |

| CRUDE SLATE | MOLECULAR DISTRIBUTION | BASIC N2 (PPM) | NA (PPM) | NI (PPM) | FE (PPM) | CU (PPM) | V (PPM) | VISCOSITY (CTS AT 122) |
|---|---|---|---|---|---|---|---|---|
| 1 | 5.5 | 42 | 2 | 8 | 7 | 6.9 | 5 | 1.8 |
| 2 | 6.4 | 385 | 2 | 1 | 14 | 0.0 | 1 | 3.5 |
| 3 | 6.5 | 140 | 1 | 1 | 6 | 0.1 | 3 | 2.7 |
| 4 | 6.4 | 403 | 2 | 36 | 2 | 0.2 | 73 | 6.3 |
| 5 | 6.4 | 210 | 3 | 2 | 28 | 0.1 | 4 | 2.5 |
| 6 | 5.6 | 193 | 3 | 3 | 4 | 0.2 | 5 | 2.8 |
| 7 | 6.3 | 413 | 8 | 7 | 20 | 0.2 | 25 | 3.8 |
| 8 | 6.1 | 90 | 13 | 1 | 11 | 0.3 | 1 | 3.0 |
| 9 | 6.3 | 314 | 2 | 3 | 10 | 0.5 | 2 | 20.0 |
| 10 | 6.8 | 790 | 3 | 24 | 7 | 0.5 | 95 | 200.0 |
| 11 | | 576 | 2 | 7 | 7 | 0.1 | 4 | 9.9 |
| 12 | 8.0 | 70 | 20 | 18 | 6 | 0.2 | 54 | 42.1 |
| 13 | 7.5 | 525 | 2 | 19 | 13 | 0.3 | 103 | 15.6 |
| 14 | 6.7 | 315 | 1 | 4 | 15 | 0.4 | 11 | 20.2 |
| 15 | 6.4 | 298 | 1 | 5 | 6 | 0.1 | 4 | 5.9 |
| 16 | 5.6 | 240 | 2 | 0 | 2 | 0.1 | 1 | 1.9 |
| 17 | 6.6 | 385 | 0 | 17 | 3 | 0.1 | 68 | 48.0 |
| 18 | 6.6 | 400 | 1 | 14 | 3 | 1.1 | 54 | 38.0 |
| 19 | 6.9 | 586 | 1 | 26 | 4 | 1.0 | 148 | 21.0 |
| 20 | 6.2 | 553 | 23 | 34 | 10 | 0.4 | 70 | 15.3 |
| 21 | 7.3 | 1848 | 0 | 37 | 23 | 0.5 | 45 | 507.3 |
| 22 | 5.8 | 193 | 3 | 2 | 18 | 0.1 | 1 | 4.9 |
| 23 | 6.4 | 175 | 2 | 1 | 2 | 0.1 | 1 | 18.3 |
| 24 | 6.7 | 200 | 2 | 2 | 14 | 0.3 | 1 | 25.0 |
| 25 | 6.6 | 1 | 1 | 28 | 6 | 31.0 | 9 | 22.0 |
| 26 | 6.5 | 245 | 1 | 27 | 5 | 198.0 | 1 | 3.8 |
| 27 | 6.5 | 260 | 3 | 1 | 19 | 0.9 | 3 | 5.3 |
| 28 | 7.0 | 525 | 1 | 11 | 6 | 0.2 | 24 | 10.5 |
| 29 | 6.5 | 1925 | 2 | 7 | 7 | 0.2 | 7 | 21.0 |
| 30 | 7.0 | 455 | 0 | 11 | 1 | 0.2 | 27 | 9.9 |
| 31 | 7.1 | 753 | 3 | 70 | 7 | 0.2 | 63 | 47.1 |
| 32 | 6.1 | 140 | 0 | 3 | 3 | 0.1 | 1 | 2.9 |

EXAMPLE 7

Figure 4:
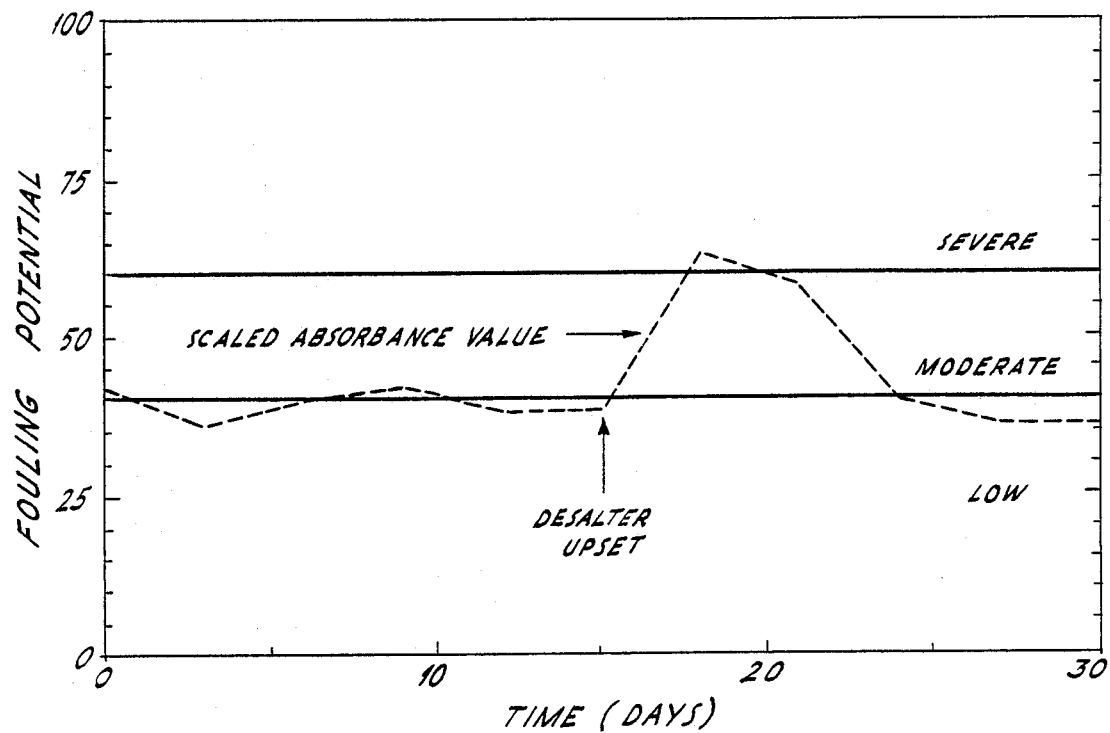

Feedstock and operating parameters for a refinery, using moderate severity fouling crude, were fairly predictable, until high fouling conditions were brought about by a desalter outage. By monitoring the absorbance at 254 nm and adjusting the amount of antifoulant added, the operators of the refinery were able to bring fouling potential back into the usual range. These results are shown in FIG. 4. Heretofore, desalter outages or other upset conditions have caused irreversible heat transfer decay, which is accompanied by increases in fuel consumption and maintenance costs and by unacceptable variations in the product stream. This experiment shows that the testing method of this method permits successful adjustment of operating conditions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for determining the fouling tendency of a crude petroleum oil, comprising the steps of:
   (a) mixing a selected volume of crude petroleum oil sample with a selected volume of a solvent medium,
   (b) agitating the resulting mixture to solubilize fouling-determining materials in the solvent medium,
   (c) removing a sample of the resulting solvent medium,
   (d) determining the absorbance of the resulting solvent medium at 230-270 nm and subtracting from the absorbance that of control solvent medium to obtain corrected absorbance of the resulting solvent medium and
   (e) determining the fouling tendency of the crude petroleum oil sample by correlating the corrected absorbance of the resulting solvent medium with calibration data specific for the solvent medium used, the ratio of oil sample to solvent and the wavelength at which absorbance is determined.

2. The process of claim 1, wherein the calibration data is derived from absorbance of a low-fouling standard crude petroleum oil and wherein scaled absorbence is determined, said scaled absorbance being equal to $$100 - [(\text{absorbance of crude petroleum oil sample})/(\text{absorbance of low-fouling standard sample})] \times 100.$$

3. The process of claim 1, wherein the solvent medium has low absorbance at 230–270 nm.

4. The process of claim 1, wherein the solvent medium is acetonitrile.

5. The process of claim 1, wherein the solvent medium contains 1–50% by volume of water and 99–50% by volume of acetonitrile.

6. The process of claim 1, wherein the solvent medium is isooctane.

7. The process of claim 1, wherein the solvent medium contains 1–50% by volume of water and 99–50% by volume of methanol.

8. The process of claim 1, wherein the ratio of volumes of crude petroleum oil sample to solvent medium is 1;10 to 1:100,000.

9. The process of claim 1, wherein absorbance is determined at 254 nm.

10. The process of claim 1, wherein agitation is accomplished by shaking the mixture.

11. The process of claim 1, wherein separation is accomplished by centrifuging the mixture.

12. The process of claim 1, wherein the solvent medium is acetonitrile; the ratio of crude petroleum oil sample to solvent medium is 1:10 to 1:100,000 by volume; agitation is accomplished by shaking; separation is accomplished by centrifugation and absorbance is determined at 254 nm.

13. In the process of refining a crude petroleum oil feed, containing varying amounts of fouling-inducing contaminants, the improvements comprising:

(a) mixing a selected volume of crude petroleum oil sample with a selected volume of solvent medium;

(b) agitating the resulting mixture to solublize fouling-determining materials in the solvent medium;

(e) removing a sample of the resulting solvent medium;

(d) determining the absorbance of the resulting solvent medium at 230–270 nm and subtracting from the absorbance that of control solvent medium to obtain corrected absorbance for the resulting solvent medium;

(e) determining the fouling tendency of the crude petroleum oil sample by correlating the corrected absorbance of the resulting solvent medium with calibration data specific for the solvent medium used, the ratio of oil sample to solvent medium and the wavelength at which absorbance is determined;

(f) adding to the feed sufficient antifouling agent to compensate for the fouling tendency, determined in step (e); and (g) refining the thus-treated feed.

14. The process of claim 13, wherein the calibration data is derived from absorbance of a low-fouling standard crude petroleum oil and wherein scaled absorbance is determined, said scaled absorbance being equal to $$100 - [(\text{absorbance of crude petroleum oil sample})/(\text{absorbance of low-fouling standard sample})] \times 100.$$

15. The process of claim 13, wherein the solvent medium has low absorbance at 230–270 nm.

16. The process of claim 13, wherein the solvent medium is acetonitrile.

17. The process of claim 13, wherein the solvent medium is isooctane.

18. The process of claim 13, wherein the solvent medium contains 1–50% by volume of water and 99–50% by volume of acetonitrile.

19. The process of claim 13, wherein the solvent medium contains 1–50% by volume of water and 99–50% by volume of methanol.

20. The process of claim 13, wherein agitation is accomplished by shaking

21. The process of claim 13, wherein separation is accomplished by centrifugation.

22. The process of claim 13, wherein absorbance is determined at 254 nm.

23. The process of claim 13, wherein the solvent medium is acetonitrile; the ratio of crude petroleum oil sample to solvent medium is 1:10 to 1:100,000; agitation is accomplished by shaking; separating is accomplished by centrifugation and absorbance is determined at 254 nm.

24. The process of claim 13, repeated at periodic intervals during refining of the crude petroleum oil feed.

* * * * *